(12) United States Patent
Broadnax

(10) Patent No.: US 6,418,188 B1
(45) Date of Patent: Jul. 9, 2002

(54) RADIATION BREAST CUP AND METHOD

(76) Inventor: Juanita L. Broadnax, 2 Clark Ct., Greensboro, NC (US) 27406

( * ) Notice: Subject to any disclaimer, the term of this patent is extended or adjusted under 35 U.S.C. 154(b) by 0 days.

(21) Appl. No.: 09/880,641

(22) Filed: Jun. 14, 2001

(51) Int. Cl.[7] ................................ A61B 6/04
(52) U.S. Cl. ........................... 378/37; 378/208
(58) Field of Search ............................ 378/37, 208

(56) References Cited

U.S. PATENT DOCUMENTS

| | | | |
|---|---|---|---|
| 3,556,081 A | 1/1971 | Jones | |
| 4,212,306 A | 7/1980 | Mahmud | |
| D348,618 S | 7/1994 | Leslie et al. | |
| 5,427,563 A | 6/1995 | Manning | |
| 6,146,377 A | * 11/2000 | Lee et al. | 600/414 |
| 6,206,843 B1 | * 3/2001 | Iger et al. | 601/2 |
| 6,254,614 B1 | * 7/2001 | Jesseph | 600/562 |

* cited by examiner

*Primary Examiner*—David P. Porta
*Assistant Examiner*—Pamela R. Hobden

(57) ABSTRACT

A breast cup is described herein which is made from a stretchable material for compressing the breast during x-ray imaging. The breast cup is constructed preferably of a fabric having elastomeric yarns to allow it to be easily worn during radiation and afterwards removed with minimal effort. The stretchable qualities provide the needed compression throughout the cup, yet is not unduly uncomfortable while worn.

17 Claims, 3 Drawing Sheets

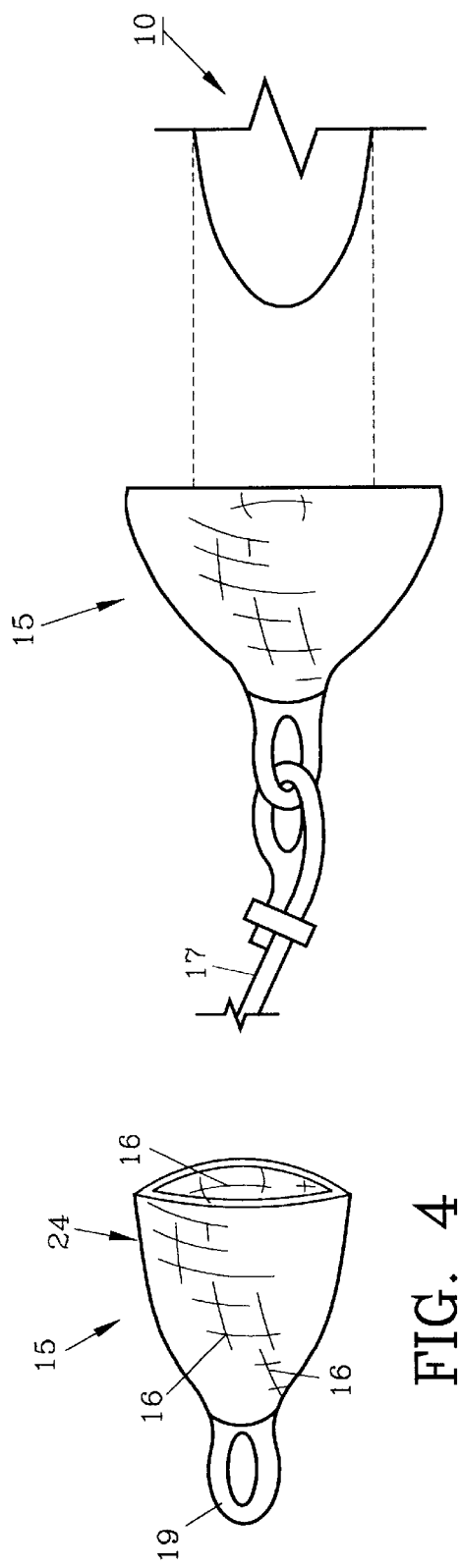
FIG. 5
FIG. 4
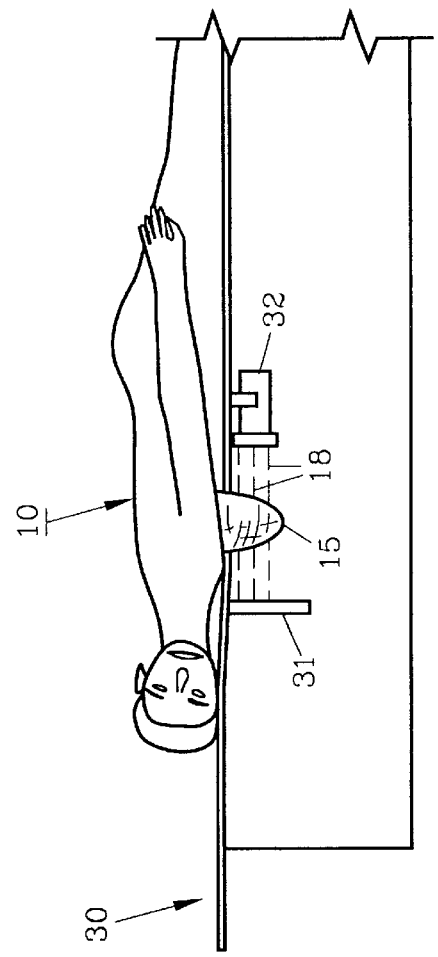
FIG. 3

RADIATION BREAST CUP AND METHOD

FIELD OF THE INVENTION

The invention herein pertains to radiation imaging procedures as are used in mammography and specifically pertains to a breast cup which can be used to x-ray the breast without undue discomfort and can be easily expanded/contracted to fit various breast sizes.

DESCRIPTION OF THE PRIOR ART AND OBJECTIVES OF THE INVENTION

X-ray imaging and other types of radiation therapy have become increasingly common in recent years. Tumors and other tissue changes which may become cancerous are often detected through images made by such techniques. Mammography is a popular procedure which requires the breast tissues to be compressed, usually between one or more plates during radiation. While such compression is necessary for a better image, such plates and procedures are extremely uncomfortable for the patient and prevent, or at least discourage, such examinations for many. Sometimes delays in obtaining radiation examinations cause greatly advanced adverse conditions which may be detected too late. Thus, as breast tissues require compression for well-defined images, it is an objective of the present invention to provide a method of compressing the breast tissue which is less painful and uncomfortable than conventional techniques.

It is another objective of the present invention to provide a stretchable breast cup which can be easily fitted to allow even pressure for a clear, readable and usable x-ray.

It is also an objective of the present invention to provide a breast cup which is formed from a stretchable material such as a fabric employing elastomeric yarns.

It is still another objective of the present invention to provide a breast cup which can be easily worn with little training.

It is still another objective of the present invention to provide a method of radiating the breast utilizing a stretchable cup for compression purposes.

Various other objectives and advantages of the present invention will become apparent to those skilled in the art as a more detailed description is set forth below.

SUMMARY OF THE INVENTION

The aforesaid and other objectives are realized by providing a stretchable breast cup preferably formed from a fabric containing elastomeric yarns. The breast cup is made to compress the breast once it is in place. The method permits manually stretching the cup to an open position while the breast is inserted. After insertion, the cup is allowed to contract thereby uniformly compressing the breast. Unlike plates that are used for compression purposes, the breast cup herein provides 360° compression and accommodates imaging from various locations therearound for a better, more complete image or model. After radiation, the breast cup can again be manually expanded or stretched to an open position for easy removal. While the invention herein is preferably used for x-ray imaging, it can also be used for ultrasonics, MRI's and other radiation type therapy. Also mechanical application and removal of the breast cup is anticipated.

BRIEF DESCRIPTION OF THE DRAWINGS

FIG. 3 pictures another radiation system with the patient in a prone position;

FIG. 4 illustrates the preferred form of the breast cup of the invention removed from the patient;

FIG. 5 features the breast cup of FIG. 4 in a somewhat expanded posture before placement on the patient;

DETAILED DESCRIPTION OF THE PREFERRED EMBODIMENT AND OPERATION OF THE INVENTION

Figure 1:
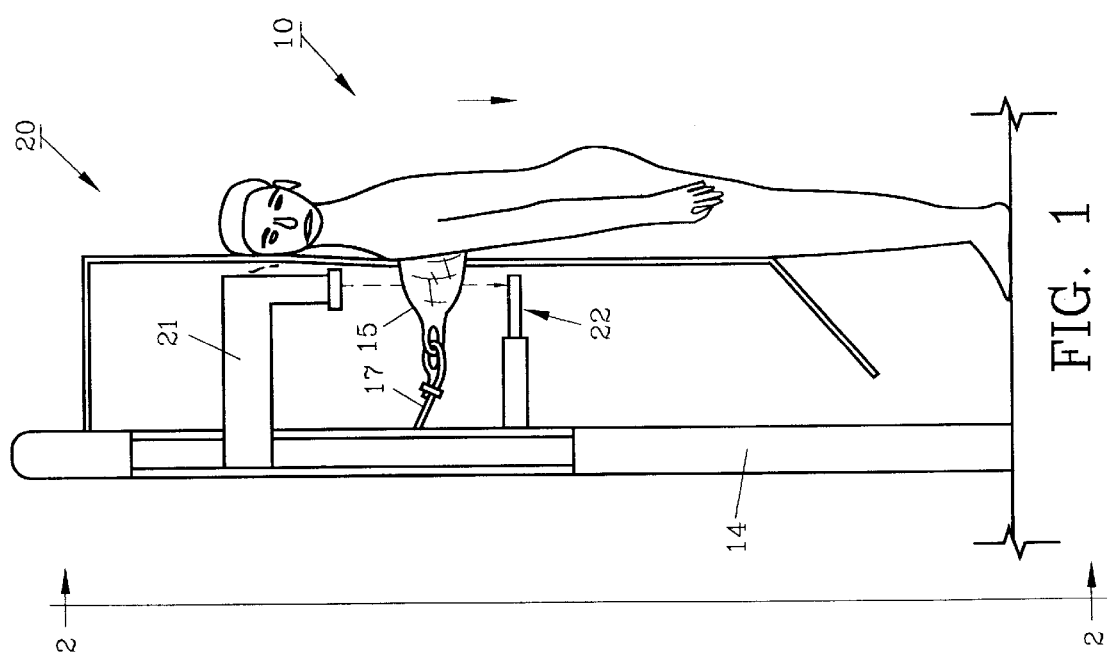
FIG. 1 demonstrates a schematic representation of a radiation system utilizing the present invention.

For a better understanding of the invention and its operation, turning now to the drawings, FIG. 1 demonstrates female patient 10 in a standing position against conventional x-ray system 20 as used in mammography. Breast cup 15 is worn by female patient 10 and it is joined to x-ray system stanchion 14 by flexible cord 17. Eyelet 19 joins breast cup 15 to cord 17 as seen in FIG. 4. As would be understood, radiation 18 passes from generator 21 through breast cup 15 to image receiver 22 which may for example, contain x-ray film, lenses or the like. Image receiver 22 is contiguous breast cup 15 as viewed in 1.

Figure 2:
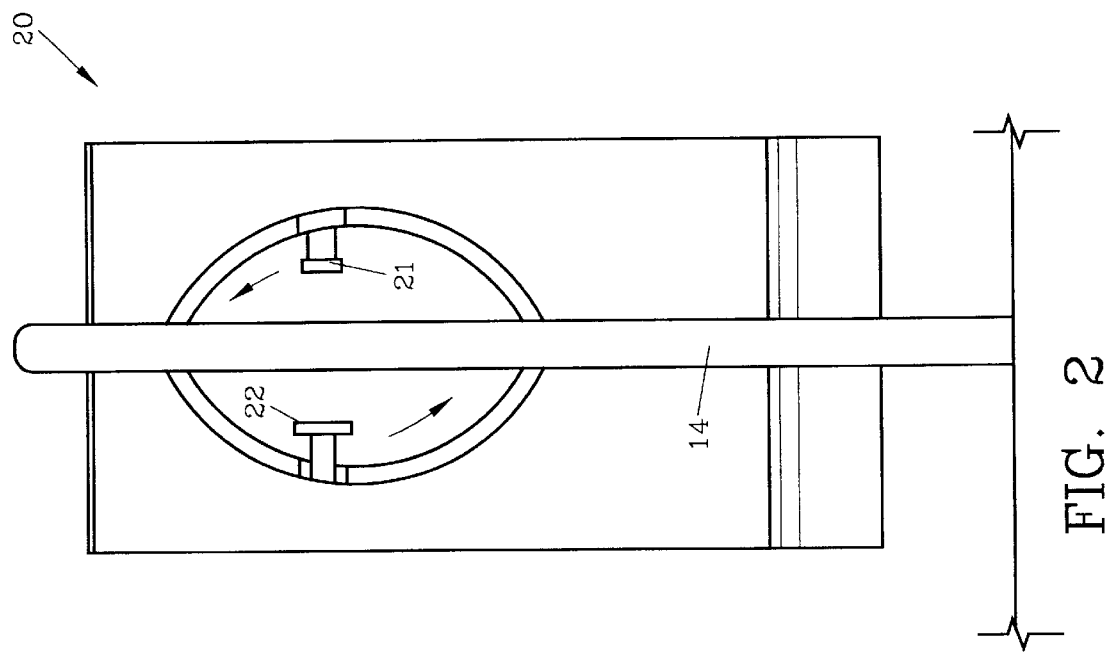
FIG. 2 shows a rear view of the radiation system as shown in FIG. 1 along line 2—2 with the x-ray generator and receiver rotated to a horizontal position.
Figure 7:
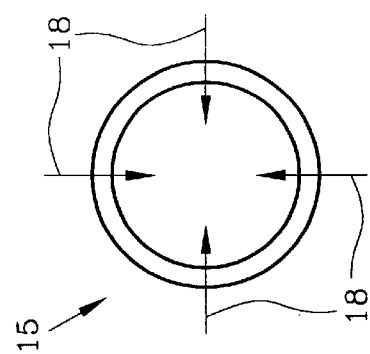
FIG. 7 shows various directions of radiation penetrating the breast cup used as seen generally along line 7—7 seen in FIG. 6.

X-ray system 20 in FIG. 2 allows x-ray generator 21 and image receiver 22 to each revolve in a somewhat circular pattern to selected locations for imaging at various angles as desired, (see also FIG. 7). FIG. 3 demonstrates female patient 10 in a prone posture on x-ray system 30 wearing breast cup 15 proximate x-ray generator 32 and image receiver 31, seen in schematic representation.

It is known that more accurate, definitive images are formed if the breast tissue is compressed during radiation. However, use of shelves, plates and the like, which are usually positioned beneath the breast while pressure is applied from above to flatten or compress the breast can cause pain and discomfort to the patient. In order to relieve the discomfort experienced by the patient, FIG. 4 demonstrates preferred breast cup 15 which is made from a conventional stretchable fabric 24 having standard elastomeric yarns 16 therein cut and sewn to a standard size. Different sizes would be available for different patients to insure that the patient utilizes breast cup 15 which when worn, compresses the breast firmly.

Figure 8:
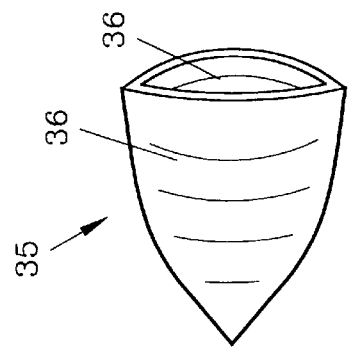
FIG. 8 demonstrates an alternate embodiment of the invention.
Figure 6:
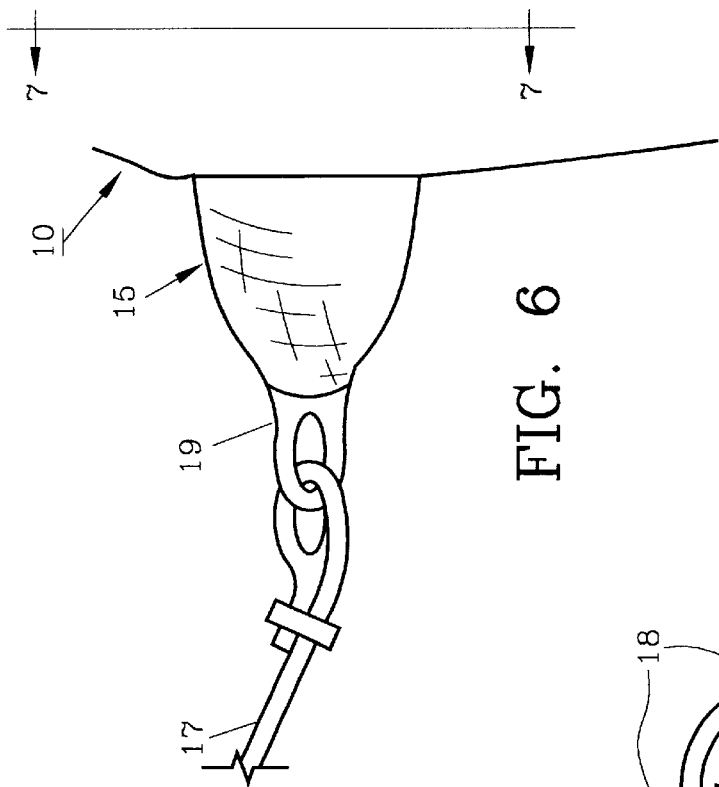
FIG. 6 depicts the breast cup in a contracted posture as worn during radiation.

The preferred method of use allows breast cup 15 to be manually expanded by placing fingers therein and opening it to a suitable size as shown in FIG. 5 and while open, inserting the breast therein. Once the breast is inserted, breast cup 15 is released whereby elastomeric yarn 16 therein will immediately contract and compress the breast completely therearound as shown in FIG. 6. The breast is thus tightly held and compressed while x-rays or other radiation pass therethrough for imaging or viewing purposes as seen in FIGS. 1 and 3. As shown in FIG. 7, x-rays 18 are passed therethrough at various angles while the breast is held in a compressed posture. Once the imaging process has been completed, breast cup 15 can again be manually expanded by grasping and opening the same whereby it is easily removed. While breast cup 15 is made from a stretchable fabric which may be knit, woven or the like to afford high compression when worn. Other stretchable materials can be utilized for an alternate embodiment of the invention such as conventional stretchable elastomeric materials including fabric or rubber. FIG. 8 shows alternate breast cup 35 as formed from a conventional synthetic elastomeric material 36 such as by molding which will stretch and compress as described above. As would be understood, various sizes of breast cup 35 would be available to insure a tight, suitable fit for the patient. Breast cup 15 may alternatively be mechanically placed on and removed from the patient.

The illustrations and examples provided herein are for explanatory purposes and are not intended to limit the scope of the appended claims.

I claim:

1. A method of radiating the breast utilizing a stretchable cup comprising the steps of:
   a) opening the cup;
   b) placing the breast in the cup;
   c) allowing the cup to close to compress the breast; and
   d) radiating the compressed breast to form an image thereof.

2. The method of claim 1 wherein opening the cup comprises the step of manually stretching the cup.

3. The method of claim 1 wherein placing the breast in the opened cup comprises the step of manually inserting the breast while the cup is held open.

4. The method of claim 1 wherein closing the cup comprises the step of allowing the cup to contract against the breast.

5. The method of claim 1 wherein radiating the breast comprises the step of radiating the breast at multiple angles for a plurality of images thereof.

6. The method of claim 1 wherein radiating the breast comprises radiating the breast with x-rays.

7. The method of claim 1 utilizing a stretchable fabric breast cup.

8. The method of claim 1 further comprising the step of positioning the patient in a standing position.

9. The method of claim 1 further comprising the step of positioning the patient in a prone position.

10. A radiation breast cup comprising: a stretchable structure, said structure being conically shaped and sized to expand to allow a breast to be inserted therein, and after insertion contractible to compress the breast therearound, and a means to attach said structure to a radiation source, said attaching means joined to said structure.

11. The radiation breast cup of claim 10 formed from a stretchable fabric.

12. The radiation breast cup of claim 11 wherein said fabric comprises an elastomeric yarn.

13. The radiation breast cup of claim 10 wherein said breast cup is formed from a stretchable polymeric material.

14. The radiation breast cup of claim 13 wherein said polymeric material comprises an elastomer.

15. The radiation breast cup of claim 10 wherein said cup is formed from rubber.

16. The radiation breast cup of claim 11 wherein said stretchable fabric comprises a knitted fabric.

17. The radiation breast cup of claim 11 wherein said stretchable fabric comprises a woven fabric.

* * * * *